United States Patent
Tafas et al.

(10) Patent No.: US 12,203,133 B2
(45) Date of Patent: Jan. 21, 2025

(54) AUTOMATED FLUORESCENCE MICROSCOPY METHOD FOR DETERMINING EFFICACY OF TREATMENT OF CANCERS AND HYPERPLASIAS

(71) Applicants: Triantafyllos P. Tafas, Rocky Hill, CT (US); Petros Tsipouras, Madison, CT (US); Michael Kilpatrick, West Hartford, CT (US); Gary Sarkis, Guilford, CT (US)

(72) Inventors: Triantafyllos P. Tafas, Rocky Hill, CT (US); Petros Tsipouras, Madison, CT (US); Michael Kilpatrick, West Hartford, CT (US); Gary Sarkis, Guilford, CT (US)

( * ) Notice: Subject to any disclaimer, the term of this patent is extended or adjusted under 35 U.S.C. 154(b) by 1344 days.

(21) Appl. No.: 16/668,476

(22) Filed: Oct. 30, 2019

(65) Prior Publication Data
US 2020/0131565 A1    Apr. 30, 2020

Related U.S. Application Data

(63) Continuation of application No. 14/931,833, filed on Nov. 3, 2015, now abandoned, which is a continuation of application No. 11/924,293, filed on Oct. 25, 2007, now abandoned.

(60) Provisional application No. 60/862,974, filed on Oct. 25, 2006.

(51) Int. Cl.
| | | |
|---|---|---|
| *C12Q 1/6841* | (2018.01) | |
| *G01N 21/64* | (2006.01) | |
| *G01N 33/574* | (2006.01) | |
| *G02B 21/00* | (2006.01) | |
| *G02B 21/16* | (2006.01) | |

(52) U.S. Cl.
CPC ....... *C12Q 1/6841* (2013.01); *G01N 21/6428* (2013.01); *G01N 21/6458* (2013.01); *G01N 33/57496* (2013.01); *G02B 21/0004* (2013.01); *G02B 21/16* (2013.01); *G01N 2021/6421* (2013.01); *G01N 2021/6439* (2013.01)

(58) Field of Classification Search
None
See application file for complete search history.

(56) References Cited

PUBLICATIONS

Chen, Xiaowei, Xiaobo Zhou, and Stephen TC Wong. "Automated segmentation, classification, and tracking of cancer cell nuclei in time-lapse microscopy." IEEE transactions on biomedical engineering 53.4 (2006): 762-766.*

Rau, Kun-Ming, et al. "Sequential circulating tumor cell counts in patients with locally advanced or metastatic hepatocellular carcinoma: monitoring the treatment response." Journal of Clinical Medicine 9.1 (2020): 188.*

Wong, Jeffrey YC, et al. "Evaluating changes in stable chromosomal translocation frequency in patients receiving radioimmunotherapy." International Journal of Radiation Oncology Biology Physics 46.3 (2000): 599-607.*

Adiga, PS Umesh. On Quantitative Evaluation of 3-D Histo-Pathological Images from Confocal Laser Scanning Microscope. Diss. Indian Statistical Institute-Kolkata, 1999.*

* cited by examiner

*Primary Examiner* — G. Steven Vanni
(74) *Attorney, Agent, or Firm* — Steven J. Moore

(57) ABSTRACT

Automated methods for detecting cancer and related hyperplasias in biological samples.

8 Claims, No Drawings

AUTOMATED FLUORESCENCE MICROSCOPY METHOD FOR DETERMINING EFFICACY OF TREATMENT OF CANCERS AND HYPERPLASIAS

This continuation utility patent application claims the benefit of priority of U.S. Non-Provisional patent application Ser. No. 11/924,293, filed Oct. 25, 2007, that claims the benefit of priority of U.S. Provisional Application No. 60/862,974 filed Oct. 25, 2006. This reference and all additional references cited in this specification, and their references, are incorporated by reference herein where appropriate for teachings of additional or alternative details, features, and/or technical background.

BACKGROUND OF THE INVENTION

1. Field of the Invention

The present invention generally relates to an automated method for detecting cancer, and dysplasias, particularly high grade dysplasias, in an individual. There is presented in one aspect a method for monitoring the effectiveness of treatment protocols in the treatment of one or more cancers.

2. Description of the Related Art

Many methods are known to aid in the microscopic analysis of samples. For example, without limitation, it is known that certain dyes have an affinity for certain cellular or subcellular structures. Such dyes may therefore be used to aid in analysis by helping to further elucidate such structures. Binding of dyes to such structures may be identified and analyzed using various techniques of microscopic detection.

Fluorescence microscopy of cells and tissues is well known in the art. Methods have been developed to image fluorescent cells in a microscope and extract information about the spatial distribution and temporal changes occurring in these cells. Some of these methods and their applications are described in an article by Taylor, et al. in American Scientist 80 (1992), p. 322-335. These methods have been designed and optimized for the preparation of a few specimens for high spatial and temporal resolution imaging measurements of distribution, amount and biochemical environment of the fluorescent reporter molecules in the cells. Detection of fluorescent signals may be by way of an epifluorescent microscope which uses emitted fluorescent light to form an image (whereas a conventional reflecting microscope uses scattered illumination light to form an image). The excitation light of a epifluorescence microscope is used to excite a fluorescent tag in the sample causing the fluorescent tag to emit fluorescent light. The advantage of an epifluorescence microscope is that the sample may be prepared such that the fluorescent molecules are preferentially attached to the biological structures of interest thereby allowing identification of such biological structures of interest.

Automated methods of conducting microscopic analysis of biological samples enhance diagnostic procedures and optimize the throughput of samples in a microscope-based diagnostic facility. Various co-owned U.S. patent applications, described more fully below, disclose aspects and embodiments of apparatuses and methods for automated microscopic analysis. These include an integrated robotic microscope system, a dynamic automated microscope operation and slide scanning system, various interchangeable objective lenses, filters, and similar elements for use in an automated microscope system, an automated microscope stage for use in an automated microscope system, an automated microscope slide cassette and slide handling system for use in an automated microscope system, an automated microscope slide loading and unloading mechanism for use in an automated microscope system, automated methods that employ computer-resident programs to drive the microscopic detection of fluorescent signals from a biological sample, useable to drive an automated microscope system, automatic operation of a microscope using computer-resident programs to drive the microscope in conducting a FISH assay for image processing.

The acronym "FISH" (fluorescence in situ hybridization) references a technique that uses fluorescent tags or labels that emit a characteristic light or color when illuminated by a light source, such as an ultraviolet or visible light source, to detect chromosomal structure. FISH uses fluorescent probes which bind only to those parts of a chromosome with which they show a high degree of sequence similarity. Such probes may be directed to specific chromosomes and specific chromosome regions. The probe has to be long enough to hybridize specifically to its target (and not to similar sequences in the genome), but not too large to impede the hybridization process, and it should be tagged directly with fluorophores. This can be done in various ways, for example nick translation and PCR using tagged nucleotides. If signal amplification is necessary to exceed the detection threshold of the microscope (which depends on many factors such as probe labelling efficiency, the kind of probe and the fluorescent dye), probes labeled with haptens such biotin or digoxygenin are used, and specific fluorescent tagged antibodies or streptavidin are bound to the hapten molecules, thus amplifying the fluorescence. The FISH technique may be used for identifying chromosomal abnormalities and gene mapping.

A commonly studied mechanism for gene overexpression in cancer cells is generally referred to as gene amplification. This is a process whereby a gene is duplicated within the chromosomes of an ancestral cell into multiple copies. The process involves unscheduled replications of the region of the chromosome comprising the gene, followed by recombination of the replicated segments back into the chromosome (Alitalo K. et al. (1986), Adv. Cancer Res. 47:235-281). As a result, 50 or more copies of the gene may be produced. The duplicated region is sometimes referred to as an "amplicon". The level of expression of the gene (that is, the amount of messenger RNA produced) escalates in the transformed cell in the same proportion as the number of copies of the gene that are made (Alitalo et al.).

Work with other oncogenes, particularly those described for neuroblastoma, suggests that gene duplication of the proto-oncogene is an event involved in the more malignant forms of cancer, and could act as a predictor of clinical outcome (reviewed by Schwab M. et al. (1990), Genes Chromosomes Cancer 1:181-193; and Alitalo et al.). In breast cancer, duplication of the erbB2 gene has been reported as correlating both with reoccurrence of the disease and decreased survival times (Slamon D. J. et al. (1987), Science 235:178-182). There is some evidence that erbB2 helps identify tumors that are responsive to adjuvant chemotherapy with cyclophosphamide, doxorubicin, and fluorouracil (Muss et al. N Engl J. Med. 1994 330(18):1260-6).

Only a proportion of the genes that can undergo gene duplication in breast cancer have been identified. First, chromosome abnormalities, such as double minute (DM) chromosomes and homogeneously stained regions (HSRs), are abundant in cancer cells. HSRs are chromosomal regions that appear in karyotype analysis with intermediate density Giemsa staining throughout their length, rather than with the normal pattern of alternating dark and light bands. They correspond to multiple gene repeats. HSRs are particularly abundant in breast cancers, showing up in 60-65% of tumors surveyed (Dutrillaux B. et al. (1990), Cancer Genet Cytogenet 49:203-217; Zafrani B. et al. (1992), Hum Pathol 23:542-547). When such regions are checked by in situ hybridization with probes for any of 16 known human oncogenes, including erbB2 and myc, only a proportion of tumors show any hybridization to HSR regions. Furthermore, only a proportion of the HSRs within each karyotype are implicated.

Second, comparative genomic hybridization (CGH) has revealed the presence of copy number increases in tumors, even in chromosomal regions outside of HSRs. CGH is a new method in which whole chromosome spreads are stained simultaneously with DNA fragments from normal cells and from cancer cells, using two different fluorochromes. The images are computer-processed for the fluorescence ratio, revealing chromosomal regions that have undergone amplification or deletion in the cancer cells (Kallioniemi A. et al. (1992), Science 258:818-821). This method was recently applied to 15 breast cancer cell lines (Kallioniemi A. et al. (1994), Proc. Natl. Acad. Sci. USA 91:2156-2160). DNA sequence copy number increases were detected in all 23 chromosome pairs.

So, C-K, et al. (Clinical Cancer Research 10: 19-27, 2004) found internal tandem duplication of cyclic AMP response element binding protein (CBP), a nuclear transcriptional coactivator protein, in esophageal squamous cell carcinoma samples from Linzhou (Linxian), China. So et al. show internal tandem duplication of the CBP gene is a frequent genetic event in human squamous cell carcinoma.

The human epidermal growth factor receptor 2 (HER-2)/neu (c-erbB-2) gene is localized to chromosome 17q and encodes a transmembrane tyrosine kinase receptor protein that is a member of the epidermal growth factor receptor (EGFR) or HER family (Ross, J S, et al., The Oncologist, Vol. 8, No. 4, 307-325, August 2003). The HER-2 gene is amplified in a fraction, perhaps 25%, of human breast cancers.

Fluorescence in situ hybridization (FISH) is commonly used for the detection of chromosomal abnormalities including sequence alterations such as single nucleotide polymorphisms or mutations found in oncogenes.

A number of methods and kits have been disclosed for screening of cancer and dysplasias, such as high grade dysplasias.

For example, ProVysion Multi-color Probe Set manufactured by Abbott Molecular is designed to detect and quantify chromosome 8, the lipoprotein lipase (LPL) gene located at 8p22, and the C-MYC gene located at the 8q24 region. Gain of 8q24 and 8p21-22 (LPL) and loss of heterozygosity are two genetic alterations that have been observed in abnormal samples. The ProVysion Multi-color Probe Set consists of three probes with three separate fluorophore labels. The multicolor probe set design is said to permit simultaneous analysis of the three genomic markers within a single cell, CEP® 8 probe labeled with SpectrumAqua, LSI LPL labeled with SpectrumOrange, and LSI C-MYC labeled with SpectrumGreen. The CEP 8 alpha satellite DNA probe hybridizes to the centromere region of chromosome 8 (8 p11.1-q11.1) and provides a mechanism for the identification of copy number of chromosome 8. The LSI LPL hybridizes to the LPL gene at 8p22 and is approximately 170 kb in size. The LSI C-MYC Probe (an approximately 750 kb probe) hybridizes to the C-MYC gene located at 8q24. The manufacturer asserts that in a normal cell hybridized with the ProVysion Multi-color Probe Set, the expected pattern is the two orange, two green and two aqua (202G2A) signal pattern, while in an abnormal cell, combinations of copies of the three probe signals may be observed. The test kit indicates that copy numbers of more or less than two of any probe indicates chromosome or gene gain or loss, respectively. Less than two copies of the LSI LPL or multiple copies of the LSI C-MYC Probe relative to CEP 8 copy number indicates loss of the LPL region and gain of the C-MYC region, respectively, relative to the chromosome 8 copy number.

U.S. Patent Publication Nos. 2004/028107 and 2005/0026190 to Vysis, Inc. assert methods of using probes and probe sets for the detection of high grade dysplasia and carcinoma in cervical cells. The methods entail hybridizing one or more chromosomal probes to a biological sample and detecting the hybridization pattern of the chromosomal probes to determine whether the subject has high grade dysplasia or carcinoma. The methods encompass the use of a set of one or more probes demonstrating a vector value of about 60 or less wherein the vector value is calculated by Vector=$[(100-\text{specificity})^2+(100-\text{sensitivity})^2]^{1/2}$ The chromosomal probes may comprise probes for specific loci, such as 8q24, 3q36, Xp22, and CEP 15, or probes, for example, substantially complementary to full coding sequence for each of HPV-16, HPV-18, HPV-30, HPV-45, HPV-51, and HPV-58. The biological sample screened may be pre-screened for the presence of a cell cycle protein, such as p16 or Cyclin E, or a cell proliferation marker, such as protein Ki67 or PCNA.

U.S. Patent Publication 2006/0063194 to Abbott Molecular also discloses probe sets and methods of using probes and probe sets for the detection of cancer, particularly lung cancer. Locus specific probes and chromosome enumeration probes are used in conjunction, and the hybridization pattern of the same used to determine whether the subject has lung cancer. Chromsomal compositions are specified, for example, a probe set for determining lung cancer may comprise a 5p15 locus specific probe, a 8q24 locus specific probe, a chromosome 6 enumeration probe and a 7p12 locus specific probe.

Diagnostic FISH light dot counting has been conventionally performed manually, by a skilled microscopist. In addition to correctly identifying the dot and its color, other size and shape characteristics must be categorized to correctly identify the chromosomal condition. The analysis is made more difficult by the time constraints imposed by the phenomena. The microscopist, therefore, must be trained to perform the examination. Even under the best conditions, the process has proven to be tedious, lengthily and subject to human error.

The application of automated microscopy has the potential to overcome many of the shortcomings of the manual approach. The automatic microscope can reliably identify the fluorescent dots in a sample, accurately determine their color, categorize them based on shape and size, and perform the summary analysis necessary to determine the presence or absence of the targeted condition without the inevitable subjective factors introduced by a human operator all in a timely manner.

It should be noted that kits for the detection of cancers are typically designed to provide only a positive or negative answer—one has a particular cancer or not. While such tests may indicate the need for interventional therapy, such as chemotherapy, they are not designed to lead one in the direction of the most appropriate interventional therapy. Rather, cancer patients are often subjected to multiple therapies, and the effectiveness of therapies determined by snap-shots of the cancer status at points in time after start of the therapy. Such snap-shots may entail for example, MRI and CAT scans of the body to determine the growth or shrinkage of tumors. As such snap-shot methods may entail considerable economic costs, as well as risks in themselves (e.g., radiation exposure), such snap-shots may be taken at considerably longer intervals than might be desired given the need for rapid intervention into resolving the disease state. As set forth below, the present inventors have also recognized that the use of automated microscopy may also be used advantageously to determine not only whether a person is inflicted with a particular cancer/hyperplasia, but also as a monitoring tool for the determination of the efficacy of different interventional therapeutic approaches to the treatment of cancer/high grade hyperplasia. In one embodiment, the monitoring of therapeutic efficacy is by means of monitoring cancer/hyperplastic cells in the systemic circulation (including the vasculature and lymph system) with a decrease in number of abnormal cells associated with the cancer/hyperplasia being taken as an indication of therapeutic success, and the degree of reduction in such cells being used as a gauge of the efficacy of one therapy against another therapy.

There remains a need in the field for the automated imaging and analysis of images arising from cancer tissue samples treated with detectably labeled probes, including fluorescently labeled probes. Additionally there remains a need for convenient, rapid, hands-free automated fluorescence microscopy of such labeled samples.

SUMMARY OF THE INVENTION

Various embodiments are disclosed herein.

In one embodiment, an automated method of screening for the presence and/or extent of a pathology in a subject, the pathology characterized by an abnormal chromosomal component in a cell of the subject, comprising the steps of a) contacting a biological sample comprising cell nuclei from said subject with one or more distinguishable labeled probes directed to at least one chromosomal sequence that characterizes the abnormality under conditions that promote hybridization of the one or more probes to the at least one sequence;

b) automatically obtaining a representation of the one or more distinguishable labels hybridized to the chromosomal sequences;

c) automatically analyzing the distribution and intensity of binding of the one or more labels in the representation to determine the presence and/or extent of an abnormal chromosomal component; and d) automatically reporting results of the analysis of step c);

wherein steps b)-d) are carried out without intervention by a human

In various further embodiments of the method of screening an automated microscope system carries out one, and usually all, of the steps of automatically obtaining a representation, automatically analyzing binding, and automatically reporting results. In this method obtaining the representation and performing automated image analysis identifies nucleic acid properties characteristic of a pathology. Various targeted chromosomal abnormalities may include a single nucleotide polymorphism (SNP), a mutated sequence, or a duplicated gene or portion thereof. Chromosomal targets for a probe may include a centromere, or a target sequence of human chromosome 3 or human chromosome 7, and all or part of a TERC gene. In additional embodiments various reference probes directed to a chromosomal locus known not to be abnormal or a reference stain may be used such that the representing and analysis steps are referenced to the reference probe or stain.

In an additional embodiment an automated method of screening for an abnormality related to a cancer, a high grade hyperplasia or a high grade dysplasia in a subject, comprising the steps of:

a) obtaining a biological sample comprising nuclei from the subject, b) contacting the nuclei in the sample with a first probe bearing a first detectable label directed to a chromosomal sequence related to the abnormality under conditions that promote hybridization of the probes to targeted chromosomal loci;

c) contacting the sample under the hybridizing conditions with at least one of a detectably labeled reference probe directed to a chromosomal locus known not to be abnormal and a reference stain;

d) automatically imaging the labels bound to the chromosomal sequences, and imaging the stain if used;

e) automatically analyzing an image for the distribution and intensity of hybridized labels and stain if used; and f) automatically reporting results of the analysis of step e);

wherein steps d)-f) are performed without intervention by a human; thereby providing an assessment of the abnormality in the subject.

In an embodiment of this method of screening the nuclei are isolated from the sample, and the nuclei are deposited to form a layer of nuclei prior to the contacting step. In further embodiments an automated microscope performs at least one, and usually all, steps of automatic imaging, automatic analyzing, and automatic reporting of results. The single layer nuclei preparation may be obtained by a number of methods known in the art, for example, by appropriate processing of thin sections from paraffin-embedded tumor tissue samples. A large variety of origins for the sample obtained from the subject is envisioned in this method. In additional embodiments of this method of screening an automated microscope is used at various stages of the method, including to automatically provide the images, to obtain the image the microscope automatically optimizes the field in which the image occurs, and to obtain images from two or more planes in a field of the sample to perform the automatic analysis of the image. In various embodiments the abnormality may be a cancer, a high grade hyperplasia or a high grade dysplasia. Various abnormalities targeted by the probe may include a single nucleotide polymorphism, a mutated sequence, or a duplicated gene or portion thereof. Additionally in certain embodiments the probe targets a centromere of chromosome 3 or a centromere of chromosome 7, or a sequence that includes the TERC gene or a portion thereof.

In still a further embodiment an automated method for monitoring the efficacy over time of a course of therapy in the treatment of a cancer or high grade hyperplasia in a patient is disclosed. This method includes the steps of (a) obtaining from the patient a fluid biological sample in which cells associated with the cancer or high grade hyperplasia are found;

(b) treating the fluid biological sample or a portion thereof with one or more detectably labeled chromosomal probes having a high degree of sequence similarity to one or more chromosomal loci associated with, or whose amplification is associated with, the cancer or high grade hyperplasia, wherein the treating is carried out under conditions sufficient to enable hybridization of the probes to chromosomes in the sample;
- (c) automatically scanning the treated fluid biological sample and detecting the one or more labels bound to one or more chromosomal probes that are hybridized to any chromosomes in the sample;
- (d) automatically detecting the number of cells associated with the chromosomes hybridized to said chromosomal probes; and
- (e) automatically comparing the hybridization patterns of a label and cell number results provided in steps (c) and (d) at differing times in the therapeutic treatment course, thereby evaluating the efficacy of the therapy in the treatment of the cancer or high grade hyperplasia.

In an embodiment the monitoring is performed at intervals of 1 day, or longer. In various embodiments of this method for monitoring efficacy the fluid biological sample includes one or more of blood, lymph, urine, an effusion fluid, an epithelial scraping, a lavage fluid, aspiration fluid, and sputum. In further embodiments of this method for monitoring efficacy an automated microscope system performs at least one of the automatic scanning and the automatic detection uses an automated microscope system, as well as automatically optimizes the field scanning the sample, and further scans two or more planes in a field of the sample. In various embodiments the automated microscope system operates without intervention by a human. In still additional embodiments a probe targets at least one of a single nucleotide polymorphism (SNP), a mutated sequence, a duplicated or amplified gene or portion thereof, a centromere of chromosome 3, a centromere of chromosome 7, and a sequence comprising the TERC gene or a portion thereof.

In still further embodiments a method for the automated high throughput characterization of a chromosomal abnormality is disclosed. This method includes the steps of:
- a) providing at least one microscope slide comprising a biological sample thereon, wherein the sample is suspected of harboring the chromosomal abnormality and wherein the sample has been hybridized to at least one detectably labeled probe specific for detection of the abnormality,
- b) installing the at least one sample-bearing slide in a means for automated, reversible, placement of the slide on the stage of an automated microscope;
- c) causing the placement means automatically and reversibly to place a sample-bearing slide to be reversibly placed on the microscope stage;
- d) causing the microscope automatically to obtain at least one image of the specimen wherein the image comprises a representation of a labeled probe hybridized to a chromosome;
- e) causing the microscope automatically to analyze the image in order to characterize the abnormality;
- f) automatically reporting the results of the analysis of step (e); and
- g) automatically repeating steps (c)-(f).

In various embodiments the automated microscope operates without intervention by a human. In additional embodiments of this high throughput method the automatic microscope obtains an image automatically by optimizing the field in which the image occurs, and obtains images from two or more planes in a field of nuclei. The biological sample may originate in any of various tissues and biological fluids. Furthermore the abnormality may be a cancer, a high grade hyperplasia or a high grade dysplasia. Various abnormalities targeted by the probe used in the high throughput method may include at least one of a single nucleotide polymorphism (SNP), a mutated sequence, a duplicated or amplified gene or portion thereof, a centromere of chromosome 3, a centromere of chromosome 7, and a sequence comprising the TERC gene or a portion thereof.

A further embodiment discloses a method that includes in order: (a) hybridizing to a biological sample one or more chromosomal probes having a high degree of sequence similarity to one or more portions of chromsomic material under conditions sufficient to enable hybridization of the probes to chromosomes in the sample (if any), the probes characterized in being tagged with one or more tags detectable by a detector; (b) automatically scanning the biological sample and detecting by a detector the one or more tag(s) associated with the one or more chromosomal probes that is hybridized to any chromosomes in the sample; and (c) automatically reporting chromosomes if any in the sample which are tagged with hybridized probe and the particular probes associated with the chromosome.

In various embodiments of the methods disclosed herein the centromeric probe may be directed to chromosomes known to house loci the replication of which, or the existence of which, are associated with a particular cancer state. For example, the centromeric probe may be direct to chromosome 3 and/or chromosome 7. The locus specific probe may be for single copy sequences may likewise hybridize with loci associated with cancer, such as loci on the q am of chromosome 3. The probe itself may advantageously have a high degree of sequence similarity to one or more portions of chromosomal material associated with a locus associated with, or the amplification of which is associated with, particular cancer(s)/hyperplasias under conditions sufficient to enable hybridization of the probes to chromosomes in the sample. The probe, for example, may be a contig consisting of four overlapping BAC clones containing the TERC gene at chromosomal location 3q26. Additional centromeric or locus specific probes may be added to a probe mixture. The nuclear staining may be by way of counterstain process. The nuclear stain may be, for example, DAPI. In automatically scanning the sample, the sample may be loaded onto an automated microscope which automatically moves from one field of view to another. The microscope may be programmed or otherwise operationally configured to allow monitoring of a number of signal channels. For example, an automated microscope may scan in DAPI and other fluorescence channels (to enumerate, for example, signals for chromosome 3, locus on 3q, and other centromeric or locus specific signal). The scanned nuclei may be automatically recorded by the automated microscope, and/or may be presented to a cytogeneticist and/or pathologist, or other health care provider. Presentation may be in numerous fashions, such as in a sorted manner with the ones with the abnormal counts presented first (e.g., counts not equal to 2 of the 3q being present first). Different cancers may be detected, such as cervical cancer (using, for example, the centromeric probe for chromosome 3 and/or chromosome 7 and a locus specific probe for single copy sequences on the q arm of chromosome 3 comprising a contig consisting of four overlapping BAC clones containing the TERC gene at chromosomal location 3q26 or a portion thereof, a DAPI nuclear counterstain, and then enumerating signals for chromosome 3, locus on 3q, and finding abnormal counts of not equal of 2 of the 3q related signals).

Automatic scanning in such embodiments may be performed, for example, by an automated microscope wherein the biological specimen is placed on slides which are manually or automatically loaded onto the microscope stage, and the slide automatically scanned. Automated microscopes that may find employment in such system are such as described in other of applicant's patent applications (see below). Scanning may also be made of other substrates onto/into which the biological sample is placed. Scanning may comprise scanning the biological sample in one plane, or in more than one plane, such as, for example, two, three or more planes. By scanning in multiple planes, detection of abnormal cells, which may be rare in terms of total number of cells in the sample, may be significantly improved. The probes may make use of FISH probes in which the fluorescent signal is picked up by the detector. The probes may produce a signal with or without another input signal, e.g. they may be radioactive, or fluoresce when impinged by an activating signal (such as an appropriate wavelength of light or other electromagnetic radiation). The probes may be directed to different replication associated cancer loci, and may comprise different fluorescent tags so as to produce different signals. The detector may be selected in accordance with signal(s) which are to be produced by the tags, e.g. a fluorescence detector for detecting fluorescent tags, with the detector operatively configured to permit detection of the particular fluorescent signals produced by the fluorescent tags. Reporting may include a simple report of the particular tags associated with the particular chromosome and/or may comprise an automatic diagnostic (indicating the type of cancer associated with the particular hybridization pattern of the chromosomes). The vector value as compared to normal specimens may be selected to be less than a particular threshold, such as less than about 60, less than about 40, less than about 30, less than about 20, less than about 10, or less than about 0.500. A useful system may comprise automatic scanning and detection in multiple signal channels at once, or in a relatively short period of time (e.g., less than 1 minute) from one another. The system may be operatively configured to process each of the multiple signals in real time, simultaneously or concurrently (or a mix of the same), to allow for quick detection of chromosomal regions, and/or regional replications, which are indicative of one or more particular cancer/hyperplasia.

DETAILED DESCRIPTION OF THE INVENTION

As used herein, "tag" and "label" relate synonymously to a moiety conjugated to a probe to render the probe detectable by a particular detection method and modality.

As used herein "probe" relates generally to a substance specifically designed to bind to a cellular target, and not to bind significantly to cellular moieties or structures not intended to be a target. In several embodiments a probe may be a nucleic acid, polynucleotide or oligonucleotide whose sequence is sufficiently complementary to a target sequence in a cellular chromosome or other nucleic acid to hybridize to the latter structure under appropriate conditions. In various additional embodiments a probe may be an antibody or a portion thereof bearing a specificity determining binding site that specifically targets a cellular structure.

As used herein "representation" relates generally to any visual, graphical, numerical, or similar assembly of information that characterizes a result obtained using a particular detection method to examine a biological sample. By way of nonlimiting example, a representation includes an image of a microscopic field that includes at least a portion of a biological sample, an image further modified for example by computer driven means to convey information by attaching color values to particular features in a field, a graphical presentation characterizing particular features derived from an image of a sample, and a table of values or verbal entries characterizing features derived from an image.

As used herein "target", "targeted", "targeting" and similar words or phrases relate generally to a cellular structure to which a probe is specifically directed. A target is any structure or component that is a member of a specific binding pair constituted of the probe and the target. The probe and target have high specificity and affinity for binding to each other, and low specificity and low affinity for a probe, or for a target, respectively, not intended to be recognized. For a probe that includes a nucleic acid or at least a specific sequence of bases, a target is a complementary sequence found in chromosomal or nucleic acid components of a cell. For a probe that is an antibody or specific binding fragment thereof, a target may be an antigenic or hapten structure found in a cell. In this framework, a probe is a "targeting" moiety, and the target structure is "targeted" by the probe.

There are provided herein systems and methods for detecting and monitoring cancers and hyperplasias, particularly high grade hyperplasias, employing automated detection of signals.

In a representative embodiment, a biological sample is interrogated with one or more chromosomal probes having a detectable tag. The chromosomal probes may be selected and/or configured to have a high degree of sequence similarity to one or more portions of chromosomal material which is indicative of an element associated with a cancer or hyperplasia such as a high grade hyperplasia. The probes may be selected such that they associate with regions on the chromosome which are indicative of a cancer/hyperplasia or the amplification of which is associated with a cancer/hyperplasia. For example, multiple replications of a particular loci on a chromosome may be indicative of a cancer/hyperplasia. The tag on the probes advantageously is detectable either directly or indirectly (e.g. by binding of another detectable molecule to a portion of the tag). In one case, the tag is fluorescent, such as in FISH (fluorescent in situ hybridization). To promote hybridization between the tagged probe and the loci of interest on the chromosomal material, hybridization should be conducted under conditions sufficient for hybridization. In such embodiment, the sample is automatically scanned using a detector that can detect the tags. Automatic scanning may be by means of an automated microscope which is operatively configured to search a sample through multiple fields of view without the need for human intervention. The ability to associate the tags with particular chromosomes enables one to determine whether the hybridization profile is indicative of a cancer or hyperplasia, such as a high grade hyperplasia. Such association permits a determination of whether a cancer/hyperplasia is likely there. Optionally, the system of such embodiment may include a means, for example software, hardware, or a software/hardware combination, for automatically reporting chromosomes in the sample which are tagged with the hybridized probe and the particular probes that are associated with the chromosome. Automatic diagnosis based upon the hybridization may also be provided as part of the automated microscope system.

In another representative embodiment, there is provided a method and system for monitoring the efficacy of a therapy to treat a cancer or hyperplasia, such as a high grade hyperplasia. The monitoring can be conducted over time in order to trace the effect of the therapeutic regimen as the patient is being treated. In such embodiment, a readily available fluid sample, such as blood, lymph, and effusion fluid, a lavage fluid, or an aspiration fluid, is taken from a patient under therapy for treating the cancer and/or hyperplasia. Any sample so obtained has in it nucleated cells, including cells suspected of harboring a detectable chromosomal abnormality characteristic of a cancer or high grade hyperplasia. The sample is then treated with chromosomal probes that hybridize with specific loci or positions in the chromosomal material, for example to detect amplification associated with an abnormal sample, comprised by the fluid sample. Optionally multiple probes directed to different loci two or more of which are associated with a particular cancer/hyperplasia may be used. Use of such combinations may improve the efficiency of the detection of the cancer/hyperplasia. Such multiple probes are advantageously tagged with different tags, such as different fluorescent tags. The tags are selected to be readable by the detector associated with an automated scanning device, such as an automated microscope, which is operatively configured to repeatedly view discrete areas of the sample without human intervention. By detecting the tags associated with one or more chromosomal probes that are hybridized to chromosomes in the sample, one can determine if a hybridization pattern indicative of a cancer/hyperplasia is seen. Improvement may be had by automatically detecting the number of cells associated with the chromosomes hybridized by the chromosomal probes. That is, by judging whether the number of cells in the fluid indicative of an abnormal chromosomal complement is lower or higher than the number of cells seen at an earlier time, one may decide whether the therapy being used is being effective in the treatment of the cancer/hyperplasia being treated. The efficacy of a particular defined therapy on a particular cancer is thus based on changes in the number of cells detected in the biological sample over time. For example, if less cells are seen after treatment than before, it may be determined that the therapy is working. Different therapy may also be compared by the degree of reduction seen in such circulating abnormal cells.

In a variant of a method provided a method and system for monitoring the efficacy of a therapy to treat a cancer or hyperplasia, a patient may provide samples independently of visits to a medical or hospital facility. For example, a patient may be provided with a kit, a system, or similar equipment for obtaining a sample of blood for subsequent analysis by methods described herein. In such nonlimiting examples, a small volume of sample blood, such as one drop or a few drops, are harvested, optionally treated to prevent clotting, optionally disposed on a slide, or otherwise maintained in a state suitable for subsequent analysis. The scheduling of accumulating such samples may include daily sampling, or sampling every other day, or twice weekly, or weekly, or biweekly, or monthly, or at even greater intervals. Samples may be stored in desiccated chambers, and may be refrigerated or frozen while awaiting shipment or transfer, and subsequent analysis.

There is also described in a representative embodiment, a system/method that can be used for detection of cancers/hyperplasias, such as high degree hyperplasias that are related with the amplification of chromosome 3q. In an embodiment method, a single layer preparation of nuclei for interphase FISH hybridization is made. For example, the layer of nuclei may be obtained following appropriate processing of thin sections from paraffin-embedded tumor tissue samples to provide a nuclear smear. The nuclear smear is then stained using a centromeric probe for chromosome 3 or chromosome 7. Subsequently, previously, or concurrently, the nuclei smear is also stained with a locus specific probe for single copy sequences on the q arm of chromosome 3 which are indicative of a cancer/hyperplasia state of interest. For example, the probe can be a contig consisting of four overlapping BAC clones containing the TERC gene at chromosomal location 3q26 or a portion thereof. Other centromeric or locus specific probes can be added to the probe mixture. In one advantageous aspect, each probe is labeled with a different fluorochrome to allow for easier detection of distinct signals. Optionally the smear may be counterstained with a nuclear stain, such as DAPI. The stained smear is then applied to an automated scanning device, such as an automated microscope, and automatically scanned in DAPI and as many fluorescence channels as needed to enumerate signals for chromosome 3, locus on 3q and any other centromeric or locus specific signal. The scanned nuclei may be presented to a health care profession, such as a cytogeneticist or pathologist for review thereof. The presentation to the health care profession may be in a sorted manner, for example with the nuclei with abnormal counts (e.g., not equal to 2) of the 3q related signals being presented first. Alternatively, or in conjunction, the system may be operatively configured (e.g. by means of a program) to analyze the scanned nuclei based on pre-programmed algorithms (for example) and to provide an automated diagnostic indication to the health care provider. Such test may be use for the detection of a number of cancers, including cervical cancer.

Automated apparatuses and methods for carrying out the microscopic analysis of biological samples enhance diagnostic procedures and optimize the throughput of samples in a microscope-based diagnostic facility. A robotic microscope system is described in co-owned U.S. patent application Ser. No. 11/833,203 filed Aug. 2, 2007. Among its disclosures, an integrated microscope system displaceable along a second surface is provided. The integrated microscope system includes an automated robotic microscope system housed in a light-tight enclosure. In this system, the automated robotic microscope system includes (i) a microscope having a stage; (ii) at least one specimen slide positionable on the stage; (iii) a light source that illuminates the slide; (iv) an image capture device that captures an image of the specimen; and (v) electrical, electronic and/or computer-driven means communicating with and controlling positioning of said specimen slide, said light source, and said image capture device. Furthermore, in this system the light-tight enclosure includes at least one shelf interior to said enclosure, wherein said automated robotic microscope system is positioned on a shelf; and a viewing monitor capable of displaying images or representations of a microscopic field being viewed or analyzed that is disposed in a surface of said enclosure viewable from a location exterior to the enclosure.

A dynamic automated microscope operation and slide scanning system is described in co-owned U.S. patent application Ser. No. 11/833,594 filed Aug. 3, 2007. Embodiments disclosed include an automated microscope and method for dynamically scanning a specimen mounted on a microscope slide using a dynamic scanning microscope incorporating a microscope slide stage, at least one source of illumination energy, at least one electronic imaging device, at least one interchangeable component carousel and a synchronization controller. An exemplary automated microscope has the ability to significantly reduce the time required to perform an examination, reduce vibration reaching the system, and to provide diagnostic results. During the imaging process, the stage and color filter wheel are in constant motion rather than stationary as in previous approaches. Real time position sensors on each of the moving sub-systems accurately telemeter the instant position of the stage mounted slide and the color filter wheel. The color filter wheel rotates at a sufficient speed to allow the capture of images, at each of the filter wavelengths, at each imaging location and focal plane.

Interchangeable objective lenses, filters, and similar elements for use in an automated microscope system are described in co-owned U.S. patent application Ser. No. 11/833,154 filed Aug. 2, 2007. This application generally relates to remotely operated or robotically controlled microscopes, and specifically to the mechanization of a means for automatically interchanging objective lens assemblies, filters and/or other optical components. An apparatus for interchanging optical components in an optical path is disclosed, which includes a control motor having a rotatable motor shaft; a support structure supporting the control motor; a planar base defined by a periphery that is generally symmetric about a central point on the planar base, the planar base including a plurality of mounting fixtures housing a plurality of optical components equi-angularly placed at a same distance from the base center, and a mechanism that causes generally symmetric rotation of the planar base about its center, so that a particular optical component of choice is positioned in the optical beam.

An automated microscope stage for use in an automated microscope system is described in co-owned U.S. patent application Ser. No. 11/833,183 filed Aug. 2, 2007. This application generally relates to a microscope stage that is adjustably moveable along the optic axis of the microscope. For example, a microscope slide mount is disclosed that is adjustable along a direction of the optic axis of the microscope, including a base plate; a microscope stage assembly movably mounted on said base plate operably configured to permit displacement of the assembly along the direction of the optic axis; and a microscope slide holding means fixed to said microscope stage assembly.

An automated microscope slide cassette and slide handling system for use in an automated microscope system is disclosed in co-owned U.S. patent application Ser. No. 11/833,517 filed Aug. 3, 2007. This application discloses a mechanism for removing and replacing a slide housed in a cassette defining a plurality of slots configured for holding slides in spaced parallel configuration.

An automated microscope slide loading and unloading mechanism for use in an automated microscope system is described in co-owned U.S. patent application Ser. No. 11/833,428 filed Aug. 3, 2007. An exemplary embodiment discloses a microscope slide manipulation device which includes: a base structure; a sleeve defining a through-void, the sleeve having a first end and a second end, the second end fastened to the base, and the sleeve being oriented perpendicular to the base; a longitudinal shaft symmetric about an imaginary longitudinal axis in part positioned in the sleeve through-void in a manner to permit axial and longitudinal movement of the longitudinal shaft in the sleeve through-void, the longitudinal shaft having a shaft first end and a shaft second end, the shaft second end positioned within the sleeve through-void and the shaft first end projecting beyond the sleeve first end and including a parallel track structure in a plane to the sleeve imaginary longitudinal axis; a plate slideably positioned between the parallel track structures on the sleeve first end, the plate having a first plate end and a second plate end, one of the first plate end or second plate end having a two-pronged forked configuration defining a void area between each prong that corresponds to the width of a microscope slide, and wherein the fork has a gripping structure operatively configured to permit gripping of a microscope slide along its edges.

Automated methods that employ computer-resident programs to drive the microscopic detection of fluorescent signals from a biological sample, useable to drive an automated microscope system, are disclosed in co-owned U.S. patent application Ser. No. 11/833,849 filed Aug. 3, 2007. An exemplary method of microscopic analysis, adaptable for high throughput analysis of multiple samples, disclosed therein includes steps of providing an automated microscope comprising a slide stage, at least one objective lens, image capturing means, programmable means for operating the microscope according to a protocol, and programmable means for providing an analytical outcome; providing a microscope slide containing a sample and interrogatable data thereon, wherein the interrogatable data provide information related to a protocol for analysis of said sample; interrogating the data; positioning the slide on the slide stage; causing the microscope to analyze the sample in accordance with the analytical protocol encoded in the interrogatable data; and causing the microscope to provide an analytical outcome representing the sample. Automatic operation of a microscope using computer-resident programs to drive the microscope in conducting a FISH assay for image processing is described in co-owned U.S. patent application Ser. No. 11/833,204 filed Aug. 2, 2007. Embodiments are disclosed which perform various image processing functions that may be employed to implement an automated fluorescence in situ hybridization method. The embodiments include an auto-exposure method for acceptably imaging all regions of the sample over an intensity range exceeding the dynamic range of the digital electronics; a method for enumeration of fluorescence in situ hybridization objects-of-interest which locates targets within the sample; nuclei identification which is a method for classifying and characterizing the objects-of-interest enumerated; segmenting nuclei which, is a method for defining the shape of an identified object of interest. Embodiments of the method are useful to characterize cell nuclei, or to enumerate a chromosome.

The automated microscope system described in the preceding paragraphs operates under control of computer-resident and computer-implemented instructions. Accordingly the system permits automated detection and analysis of samples without human intervention. The automated slide cassette and automated slide loading and unloading mechanism permit unattended high throughput analysis of a plurality of samples.

Methods disclosed herein are directed toward automating the detection and analysis of tissue specimens whose cells are suspected of harboring genes that have undergone somatic gene duplication or gene amplification during carcinogenesis. The methods afford computer driven image accumulation, and computer driven analysis of images obtained, as well as reporting results of such analyses in a variety of formats in an automated procedure that frees the methods from human intervention to a significant extent. Reports may be presented, by way of nonlimiting example, in the form of charts, tables, images of representations of a field on a slide, and the like. Reports are in digital formats as files or records, and as such are conveniently disseminated to local or remote locations for review. Because of the use of automated fluorescence microscopy, such as a system including components and software that is referenced herein, rapid, convenient, and accurate screening of tissue samples is afforded. These methods, and the automated microscope system employed in implementing them, are particularly well suited for use in high throughput analysis of a plurality of tissue samples.

Tissue samples may be derived from medical or surgical procedures that yield specimens from suspect tissues or organs, including by way of nonlimiting example scrapings from epithelial surfaces, surgical excision of epithelial tissues, various biopsies, and surgically resected tissues and organs. In nonlimiting embodiments, such samples are fixed and embedded in a supporting material, and tissue slices thereof are prepared in a microtome or similar instrument. The tissue slices are mounted on microscope slides. Additionally samples for analysis may originate from a biopsy, blood, lymph, urine, an effusion fluid, a biological fluid, a lavage fluid, aspiration fluid, sputum, and a tissue.

In various embodiments a slide-mounted tissue slice is then treated with a generic fluorescent dye that stains chromosomes or nucleic acids with a fluorescent probe having a particular emission color isolatable by a suitable optical filter. A nonlimiting example of a generic dye is 4',6-diamidino-2-phenylindole (DAPI). Staining with DAPI affords a means of identifying the location of nuclei, or of chromosomes, for the computer driven process of image capture for further capture of images from FISH probes.

The tissue specimen is hybridized to a fluorescently labeled FISH probe whose nucleotide sequence is constructed specifically to target a gene sequence, or a segment or portion of a gene sequence, that is specific for an oncogene sought to be targeted. The various fluorescent labels used in the probes are optically isolatable by the use of suitable filters and related optical components. The specificity of the nucleotide sequence ensures that all, or most, chromosomes in a specimen having the target sequence are in fact hybridized to the probe, while non-target sequences remain unhybridized. Hybridization is caused to proceed by heating sufficiently to denature the target sequence, thereby exposing single stranded DNA complementary to the probe. The process then continues by annealing the probe to the exposed single strand, thus labeling the sequence with the fluorescent label. A worker of skill in the field of the invention knows specific conditions of solution ionic strength, buffer composition, temperature, and the like, to achieve the required hybridization. Following annealing the excess probe is rinsed away.

The slide bearing the hybridized specimen is inserted into a slide-loading cassette that is a component of the automated microscope system. The system is set into operation, at which point the slide is caused to be transported from the cassette and placed on the stage of the microscope. In many embodiments each slide may bear a code interrogatable by the automated microscope that may include information such as a specimen identification, and the identities of any generic chromosome dye, and the various fluorescent labels on the FISH probes, used with the specimen in question. Such information guides the automated microscope in selection of appropriate optical filters and related optical elements for use throughout the image accumulation process.

The automated scanning device, such as an automated microscope, may be configured to scan the biological sample in one plane, or in more than one plane, such as, for example, two, three or more planes. By scanning in multiple planes, detection of abnormal cells, which may be rare in terms of total number of cells in the sample, may be significantly improved.

In an embodiment, the probes may make use of FISH probes in which the fluorescent signal is detected by the detector. It should be understood that the probes may produce a signal with or without another input signal, e.g. they may be radioactive, or fluoresce when stimulated by an activating signal (such as an appropriate wavelength of light or other electromagnetic radiation). The probes may be directed to different replication associated cancer/hyperplasia loci, particular loci associated with a cancer/hyperplasia. Different fluorescent tags may be associated with probes to different loci so as to produce different signals.

The detector may be selected in accordance with signal(s) which are to be produced by the tags, e.g. a fluorescence detector for detecting fluorescent tags, with the detector operatively configured to permit detection of the particular fluorescent signals produced by the fluorescent tags.

Automated analysis may begin by directing the use of a low magnification of the microscope, using at least the generic dye, and possibly the probe labels, to identify regions within the specimen for imaging at a higher magnification. When the computer software identifies regions of interest at low magnification, it may direct the automated microscope to interchange objective lenses and/or filters, and any other optical components, for suitable image analysis of identified loci at higher magnification based on emitted light originating from one or another of a fluorescent label used in a probe. The computer software may then use features in an image, by way of nonlimiting example, the intensity and number of FISH-labeled spots, to enumerate such spots arising within single nuclei. Such an enumeration may provide a resulting indication of the extent of gene amplification in cells of the tissue in the specimen being analyzed.

Reporting may include a simple report of the particular tags associated with the particular chromosome and/or may comprise an automatic diagnostic (indicating the type of cancer associated with the particular hybridization pattern of the chromosomes). In certain embodiments the automated microscope system automatically generates a report detailing the findings obtained in the various images, fields and representations obtained during operation. Such reports may make use of, or may reference, historical information, or patient information, already resident in a memory device associated with the automated microscope.

A useful system may comprise automatic scanning and detection in multiple signal channels at once, or in a relatively short period of time (e.g., less than 1 minute) from one another. The system may be operatively configured to process each of the multiple signals in real time, simultaneously or concurrently (or a mix of the same), to allow for quick detection of chromosomal regions, and/or regional replications, which are indicative of one or more particular cancer.

The vector value as compared to normal specimens may be selected to be less than a particular threshold, such as less than about 60, or less than about 40, or less than about 30, or less than about 20, or less than about 10, or less than about 3, or less than about 1, or less than about 0.500.

In a nonlimiting example of an analysis procedure, the automated method may involve steps such as the following:
1. A microscopic specimen is deposited by layering on a slide a thin section from a paraffin embedded tissue.
2. The tissue section is stained using fluorescence in situ hybridization (FISH) probes for targeted chromosomal loci or sequences.
3. Following FISH probe treatment the slide is scanned using a desktop scanner at a resolution that may be set at 100, or 200, or 300, or 400 dots per inch, or more, and the scanned image is processed in order to identify an area that has been marked by a pathologist for attention. The digitized information about this area is passed to an automated fluorescence microscope, such as an Ikoniscope™ microscope system (Ikonisys, Inc., New Haven, Conn.).

4. The slide is loaded in the automated microscope.
5. Automated scanning begins by using a low magnification, such as 2×, or 4×, or 5×, or 10× magnification, or a similar low magnification, for analysis using the DAPI channel, by which the instrument detects the regions of the slide that contain nuclei. Typically, scanning is done within the marked area in step (3).
6. Then, using a higher magnification, such as 10×, or 15×, or 20×, or 40×, or even greater magnification, the microscope system scans the regions identified in the previous step. Scanning is performed in the DAPI channel for the detection of nuclei and then in a channel directed to a wavelength of light in the range emitted by the fluorescent label used in the probe, such as an orange channel, for the enumeration of, for example, orange signals from a FISH probe with a label that emits orange radiation, and in a green channel for the enumeration of signals from a FISH probe with a label that emits green radiation. These provide features of interest, such as nuclei, for further characterization.
7. The positions of features of interest are recorded for subsequent scanning and verification of signal count in a highest magnification, such as a 100× magnification.
8. The automated microscope presents all images collected during 20× and 100× scanning to the pathologist for review and also offers the possibility for subsequent rescanning of the slides if the pathologist requires review in high magnification of another slide area.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed:

1. An automated method for monitoring the an efficacy over time of a course of a treatment of a cancer or hyperplasia in a patient, said method comprising the steps of
   (a) obtaining from the patient a fluid biological sample in which cells associated with the cancer or hyperplasia are found;
   (b) treating said fluid biological sample or a portion thereof with one or more detectably labeled chromosomal probes to one or more chromosomal loci associated with, or whose amplification is associated with, said cancer or hyperplasia, under conditions sufficient to enable hybridization of said probes to chromosomes in the sample;
   (c) automatically scanning said treated fluid biological sample to obtain a digitized representation of said fluid biological sample or a portion thereof and detecting said one or more probes bound to any chromosomes in said sample by:
      irradiating said treated fluid biological sample with fluorescence-exciting illumination based on interrogatable information,
      capturing one or more images of the biological sample,
      digitizing each of the one or more images, and
      analyzing at least one one or more digitizations to cause adjustment of exposure parameters to form the digitized representation;
   (d) automatically detecting from the digitized representation a number of cells associated with said chromosomes hybridized to said chromosomal probes; and
   (e) automatically comparing hybridization patterns of one of the labeled probes of step (c) and the number of cells provided in step (d) at differing times over the course of the treatment, thereby determining the efficacy by detecting a variation in a number of abnormal cells associated with the cancer or hyperplasia.

2. The method of described in claim 1 wherein at step (e) the differing post-treatment times are separated by 1 day or greater.

3. The method described in claim 1 wherein the fluid biological sample comprises one or more of blood, lymph, urine, an effusion fluid, a lavage fluid, aspiration fluid, and sputum.

4. The method described in claim 1 wherein an automated microscope system performs steps (c)-(e) without intervention by a human.

5. The method described in claim 4 wherein the automated microscope system automatically optimizes a field scanning the sample.

6. The method described in claim 4 wherein the automated microscope scans two or more planes in a field of the sample.

7. The method described in claim 1 wherein the one or more detectably labeled chromosomal probes target at least one of a single nucleotide polymorphism (SNP), a mutated sequence, a duplicated or amplified gene or portion thereof, a centromere of chromosome 3, a centromere of chromosome 7, and a sequence comprising the TERC gene or a portion thereof.

8. The method described in claim 1 wherein the fluid biological sample in step (a) is obtained from the patient with assistance from another human.

* * * * *